United States Patent [19]

Gezari

[11] 4,065,230
[45] Dec. 27, 1977

[54] RECIPROCATING INFUSION PUMP AND DIRECTIONAL ADAPTER SET FOR USE THEREWITH

[75] Inventor: Walter A. Gezari, Killingworth, Conn.

[73] Assignee: Hart Associates, Inc., East Hartford, Conn.

[21] Appl. No.: 625,581

[22] Filed: Oct. 24, 1975

Related U.S. Application Data

[63] Continuation-in-part of Ser. No. 541,882, Jan. 17, 1975, abandoned.

[51] Int. Cl.² .......................... F04B 9/08; F04B 35/02
[52] U.S. Cl. ................................... 417/317; 417/342; 417/507; 417/515; 128/214 F
[58] Field of Search ............... 417/317, 515, 507, 342, 417/63; 128/214 F

[56] References Cited

U.S. PATENT DOCUMENTS

| | | | |
|---|---|---|---|
| 2,565,255 | 8/1951 | Morine | 417/515 |
| 2,843,050 | 7/1958 | Harper | 417/317 |
| 2,998,781 | 9/1961 | Triebel | 417/317 |
| 3,205,906 | 9/1965 | Wilkinson | 417/507 |
| 3,451,393 | 6/1969 | Sarnoff | 128/214 F |
| 3,474,965 | 10/1969 | Coleman | 417/342 |
| 3,516,761 | 6/1970 | Scooggins | 417/342 |
| 3,536,451 | 10/1970 | Ludwin | 417/63 |
| 3,554,673 | 1/1971 | Schwartz | 417/515 |
| 3,718,409 | 2/1973 | Brandenberg | 417/342 |
| 3,731,679 | 5/1973 | Wilhelmson | 128/214 F |

*Primary Examiner*—William L. Freeh

[57] ABSTRACT

A reciprocating infusion pump is presented having a pair of syringes activated by individual actuating cylinders. The actuating cylinders are interconnected with a hydraulic fluid, and the cylinders and alternately pneumatically actuated whereby the cylinders alternately act as drive and follower cylinders whereby one syringe delivers fluid to a patient while the other is refilled from a reservoir. A directional adapter set is affirmatively actuated in synchronism with the actuating cylinders to control the direction of fluid flow from the reservoir to the syringes and from the syringes to the patient.

18 Claims, 10 Drawing Figures

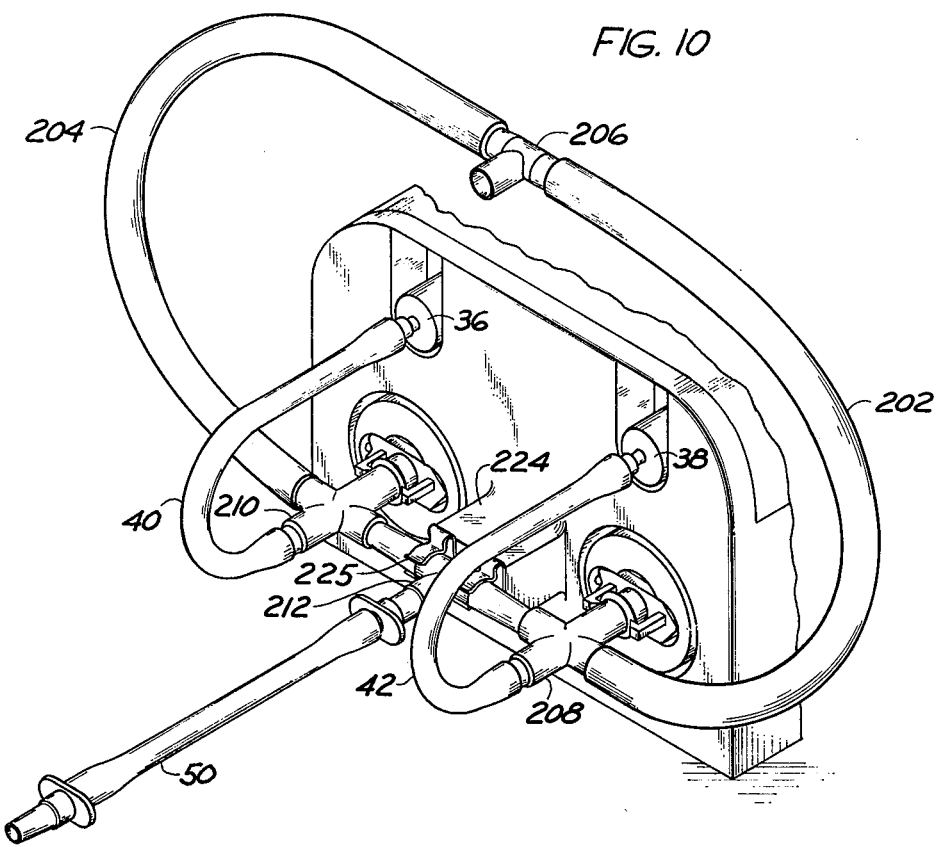
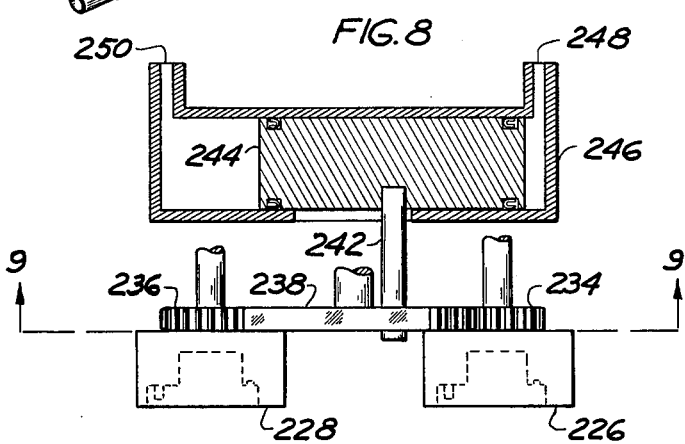
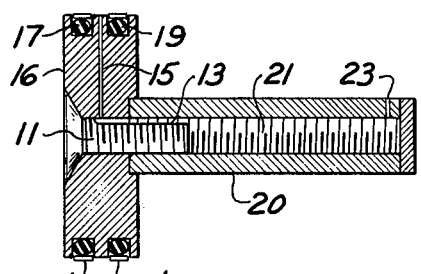
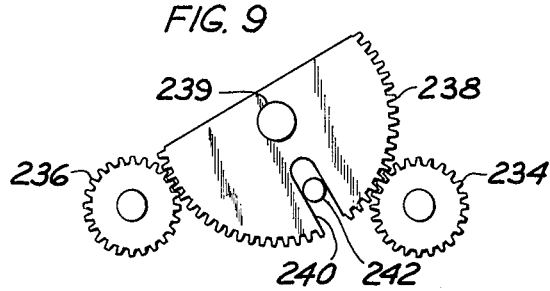

RECIPROCATING INFUSION PUMP AND DIRECTIONAL ADAPTER SET FOR USE THEREWITH

CROSS-REFERENCE TO RELATED APPLICATION

This application is a continuation-in-part of my application Ser. No. 541,882, filed Jan. 17, 1975 now abandoned.

BACKGROUND OF THE INVENTION

This invention relates to the field of feed control systems for fluids. More particularly this invention relates to a reciprocating infusion pump.

Infusion pumps find widespread use in the medical and research fields. Accurate and reproducible flow rates, compact size, and the ability to vary flow rates over a wide range are all very important considerations for such devices; and many of the prior art devices are deficient in one or more of these features.

Typical commercially available infusion pumps are electrically operated, and this is especially true for reciprocating infusion pumps. These pumps suffer from one or more of the deficiencies noted above; and in addition may be undesirable for use in operating rooms and other environments where oxygen is used because of fire and explosion hazards from electrical arcing. Another problem with reciprocal infusion pumps relates to the need to control the direction of fluid flow from a reservoir to the syringes and from the syringes to the patient. Positive control of flow direction has not ordinarily been available for infusion pump devices.

Many prior art hydraulic control devices of general industrial types have incorporated what is known as a hydro-check control feature. Such devices have a pair of actuating cylinders arranged either in tandem or in parallel, with a mechanical connection between the actuating element. One cylinder has hydraulic fluid on both sides of its piston, with a flow path between the opposite sides of the piston. The other cylinder has provisions for selective application of pneumatic pressure to one side or the other of its piston. In the parallel arrangement the piston rods are connected together by a link external of the cylinders; in the tandem or series arrangement the pistons are connected by an extended piston rod. In addition to being only single acting rather than reciprocating, the parallel arrangement experiences side loads, and the tandem arrangement has size problems.

SUMMARY OF THE INVENTION

As applied to reciprocating infusion pumps, the present invention overcomes or reduces the problems of the prior art and results in a novel and improved fluidic operated reciprocating infusion pump. The pump of the present invention combines pneumatic and hydraulic actuation and operation and results in an infusion pump which is reciprocal in operation, has accurate and reproducible flow rates, and can be easily adjustable to vary flow rates. The pump also synchronously operates an affirmatively actuated directional adapter set to control the direction of fluid flow from the reservoir to the syringes and from the syringes to the patient.

The pump has a pair of cylinders with hydraulic fluid on one side of each piston and provision for introducing pneumatic fluid on the other side of each piston. A fluid transfer line interconnects the hydraulic fluid chambers, and a valve in the line controls the rate of fluid flow between the cylinders. The pneumatic chambers on the opposite side of each piston are alternately pressurized and vented, whereby the pistons are driven in a reciprocating manner by the combined action of the pneumatic pressure and the transfer of hydraulic fluid between the cylinders. The pistons drive the plungers of syringes to alternately charge and discharge fluid to and from the syringes. A pilot operated control valve is responsive to the travel of the pistons to switch the pneumatic pressure between the cylinders.

Each piston has an interpiston bleed with a pair of seals straddling, i.e. on opposite sides of, the bleed to isolate and prevent mixing of the hydraulic and pneumatic fluids on the opposite sides of the pistons. Any leaking hydraulic or pneumatic fluid will be vented via the interpiston bleed to prevent contamination of one fluid with the other. Also, the interpiston bleed effects a safety feature whereby the pump will cease cycling upon loss of a predetermined amount of hydraulic fluid.

A directional adapter set controls the direction of fluid flow from a reservoir to the syringes and from the syringes to the patient. The directional adapter set has a pair of three-way valves which control the flow, and these three way valves are affirmatively actuated in synchronism with the operation of the pistons by the same signal used to operate the pistons.

As a further feature, a micropore filter in the line to the patient prevents air bubbles from being delivered to the patient, thus preventing air embolism.

Accordingly, one object of the present invention is to provide a novel and improved pneumatically powered, hydraulically controlled feed control system.

Another object of the present invention is to provide a novel and improved infusion pump.

Still another object of the present invention is to provide a novel and improved fluidic operated infusion pump.

Still another object of the present invention is to provide a novel and improved reciprocating infusion pump.

Still another object of the present invention is to provide a novel and improved fluidic operated reciprocating infusion pump.

Still another object of the present invention is to provide a novel and improved fluidic operated infusion pump having operating pistons with an interpiston bleed to prevent mixing of two fluids.

Still another object of the present invention is to provide a novel and improved reciprocating infusion pump having a directional adapter set operated in synchronism with the reciprocation of the pump.

Other objects and advantages will be apparent to and understood by those skilled in the art from the following detailed description and drawings.

BRIEF DESCRIPTION OF THE DRAWINGS

In the drawings, wherein like elements are numbered alike in the several figures:

FIG. 3 omitting the actuator of FIGS. 8 and 9.

FIG. 5 is a detailed view of one of the pistons shown in FIG. 1.

FIG. 8 is a top plan view of the actuator for the directional adapter set.

FIG. 9 is a view along line 9—9 of FIG. 8.

FIG. 10 is a partial view similar to FIG. 2 showing the directional adapter set mounted on the front of the pump.

DESCRIPTION OF THE PREFERRED EMBODIMENT

Figure 1:
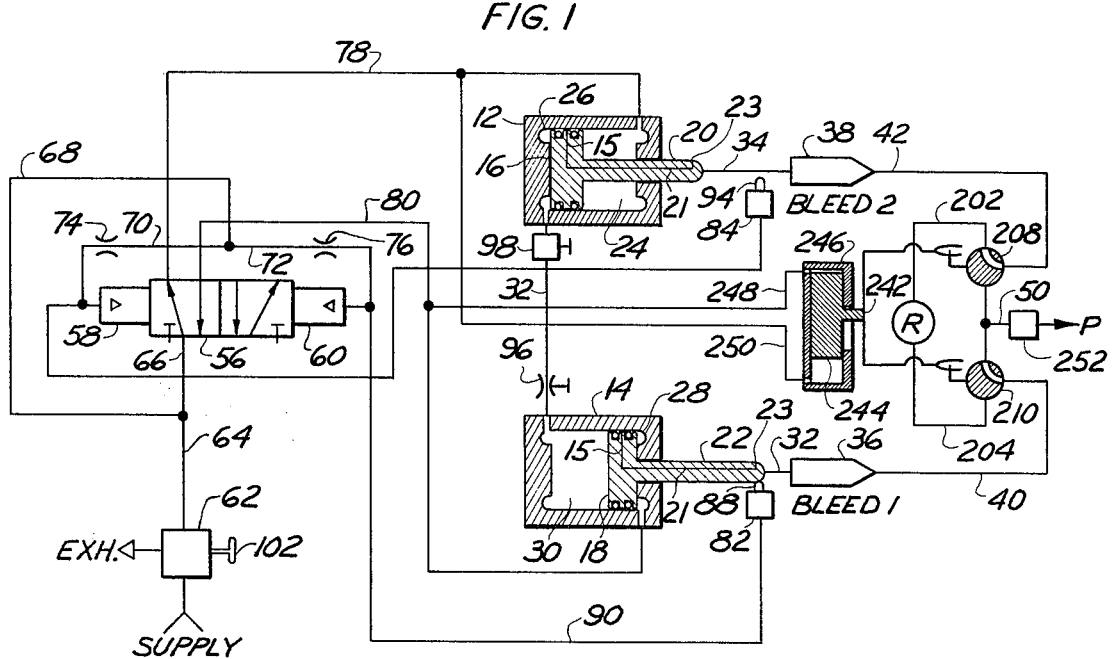
FIG. 1 is a schematic of the infusion pump, including the control system thereof, of the present invention.
Figure 2:
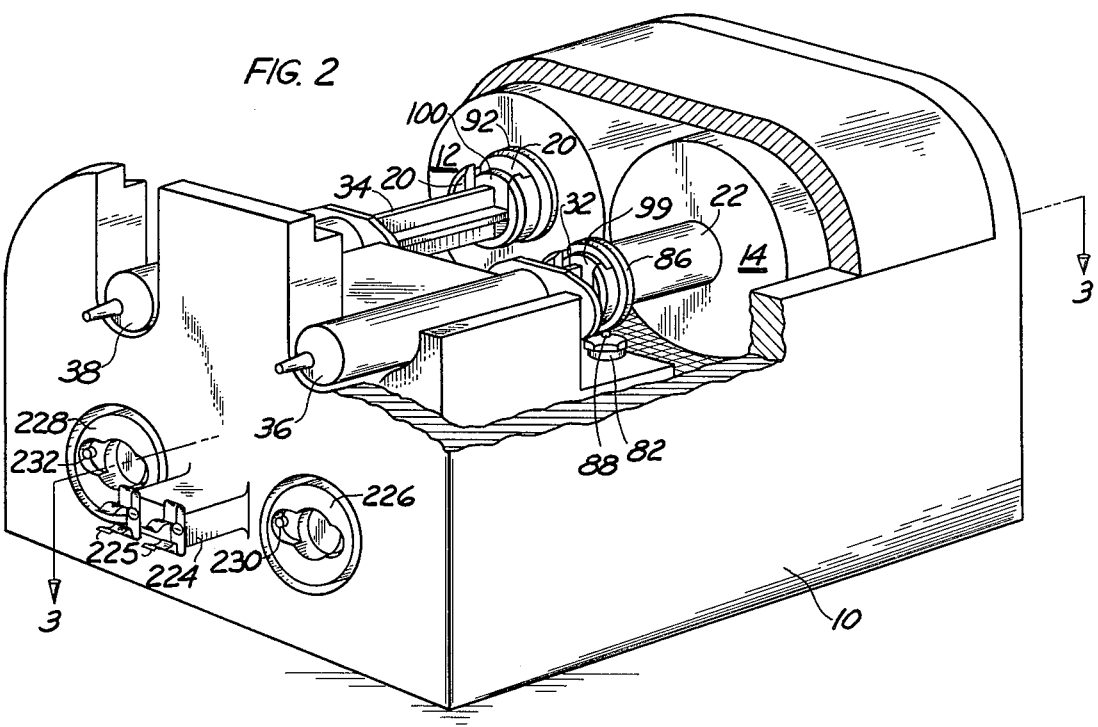
FIG. 2 is a perspective view, partly broken away, of the infusion pump of the present invention.

Referring now to FIGS. 1 and 2, the infusion pump 10 has a pair of cylinders 12 and 14. Pistons 16 and 18 are housed in the respective cylinders, and piston rods 20 and 22 extend from one side of each piston through the walls of their respective cylinders. Piston 16 is shown in its leftmost or full rear position corresponding to maximum retraction of rod 20; and piston 18 is shown in its rightmost or full forward position corresponding to full extension of rod 22. Each piston and rod is movable between the position in which it is shown and the full opposite position shown for the other piston. Piston 16 divides cylinder 12 into front and rear chambers 24 and 26 of variable volume depending on the position of piston 16; and piston 18 divides cylinder 14 into front and rear chambers 28 and 30 of variable volume depending on the position of piston 18. Rear chambers 26 and 30 are filled with an incompressible hydraulic fluid, such as oil, and hydraulic conduit 32 connects rear chambers 26 and 30 to provide fluid communication therebetween. As will be discussed in detail hereinafter, the front chambers 24 and 28 are alternately pressurized with air or other actuating pneumatic fluid and vented.

FIG. 5 shows the details of one of the pistons, e.g. piston 16, and it will be understood that the other piston (18) is identical. Each piston is connected to its rod by a screw or other fastener 11 that has a recessed flat portion 13. Each piston has a centrally located radial bleed 15 from the outer surface to the center of the piston, and the bleed 15 is straddled by a seal structure made up of a pair of annular "O" rings 17 and 19 and teflon "glyd" rings 17' and 19'. Bleed 15 is in fluid communication with a bleed passage 21 in the piston rod (recessed flat 13 permitting flow connection along screw 11). Bleed orifice 23 connects bleed passage 21 to atmosphere. The "glyd" rings 17' and 19' are low friction teflon seal rings obtainable from W. S. Shamhan Co. of Fort Wayne, Indiana, and they occupy the space between the "O" rings and the cylinder wall to provide a low friction seal against the walls of cylinders 12 and 14. Any oil which leaks from a rear chamber (26 or 30) past seal 17-17' will be bled to atmosphere thru bleed 15, passage 21 and bleed passage 23. Similarly, any pressurized air in a front chamber (24 or 28) that leaks past seal 19-19' will also be bled to atmosphere. Thus, the seals and bleed system serves to isolate the rear chambers (26 and 30) from their respective front chambers (24 and 28) and prevents any mixing or contamination of the fluids in the front and rear chambers.

Rods 20 and 22 are connected to the plungers 32 and 34 of syringes 36 and 38 (see also FIG. 2), the bodies of which are clamped in any convenient manner in the casing of pump 10. Hence, reciprocation of pistons 16 and 18 results in reciprocating action of plungers 32 and 34 whereby a first one of the syringes delivers fluid (to a patient, P, or for other end use) while the second draws fluid from a reservoir, R, and the operation is then switched whereby that second syringe delivers the fluid while the first syringe draws fluid from the reservoir.

Figure 7:
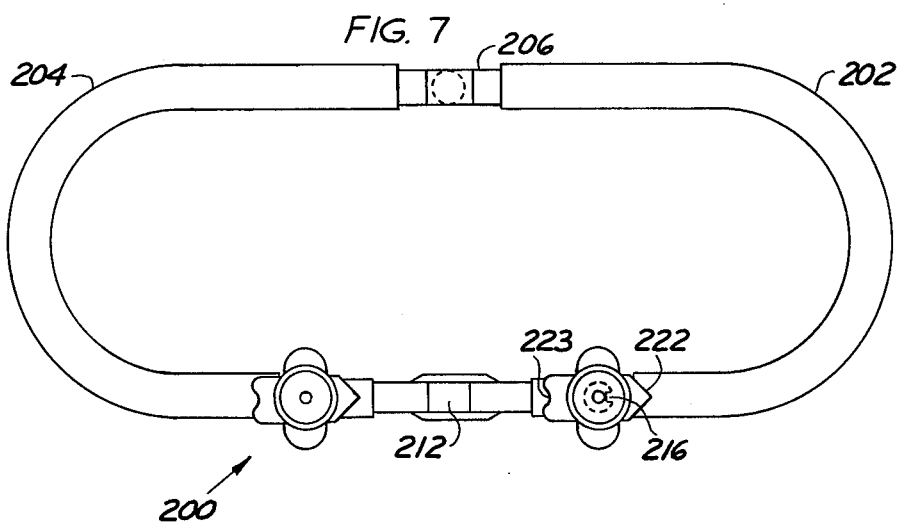
FIG. 7 is a view along line 7—7 of FIG. 6.
Figure 6:
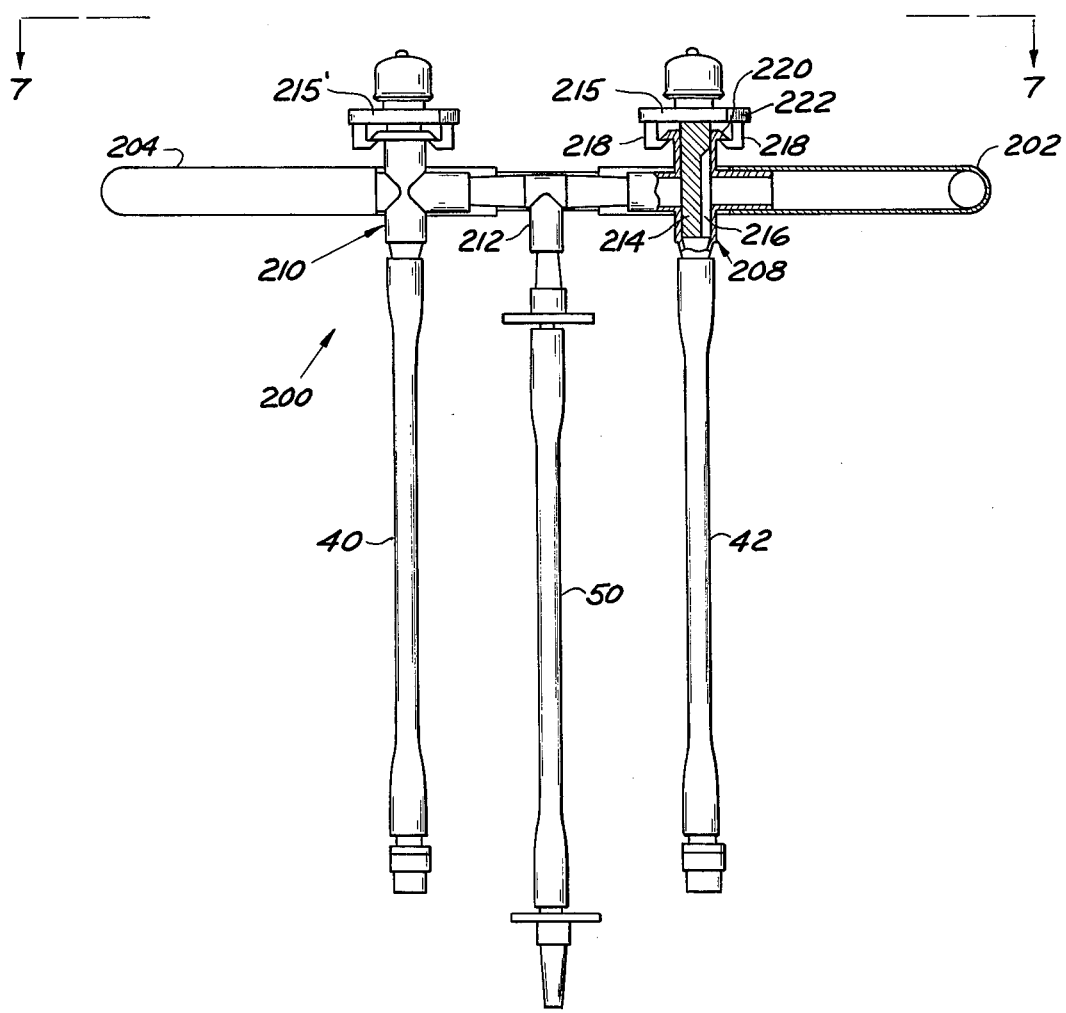
FIG. 6 is one view of the directional adapter set of the present invention.

The alternate drawing of fluid to fill one of the syringes from reservoir R while the other is delivering fluid to the patient P is accomplished through a directional adapter set 200 (see also FIGS. 6 and 7). Directional adapter set 200 has flexible plastic tube branches 202 and 204 connected to a rigid plastic "T" connection 206. The stem of T connection 206 is connected to reservoir R, and the branches are each connected to tube branches 202 and 204 respectively, to fill tube branches 202 and 204 with fluid from the reservoir. Branch 202 is connected to three way valve 208, and branch 204 is connected to three way valve 210. Valves 208 and 210 are connected, respectively, to lines 42 and 40, which are connected to syringes 38 and 36, respectively. Delivery line 50 is connected to deliver fluid to a patient P, and the three way valves 208 and 210 are connected by a rigid T connection 212 to line 50. Each of the three way valves 208 and 210 may be connected either to deliver fluid from reservoir R to its associated syringe 38 or 36 or to deliver fluid from one of the syringes to line 50 and thence to the patient. In operation, one of the three way valves will be positioned to supply fluid from the reservoir to one of the syringes, while the other three way valve will be positioned to deliver fluid from one of the syringes to the patient.

Both of the three way valves are identical, one (208) being shown in cross-section in FIG. 6. Valve 208 will be described, and a superscript will sometimes be used to indicate corresponding parts of valve 40. Each three way valve has a solid rotatable cylindrical valve element or core 214 with a groove or slot 216 on a portion of the outer face. Valve element 214 is fixed to an actuating handle 215 which has fingers 218 latched under a lip 220 on the outer housing of the valve to prevent axial movement of core 214. Valves 208 and 210 are always in flow communication with their respective lines 42 and 40, and they alternately connect the lines 42 and 40 to the reservoir or to the patient. As can best be seen in FIG. 7, handles 215 are in the form of directional arrows with the head 222 pointing in the direction of slot 216 and with a notch 223 at the opposite end. Hence, the arrow head 222 points in the direction of the lines with which the lines 42 and 40 are in flow communication by the position of the respective three way valves. Thus, as shown in FIG. 6, valve 208 has established flow communication between reservoir R and syringe 38 via lines 202 and 42, and it has blocked off flow communication between syringe 38 and patient delivery line 50; and valve 210 has established flow communication between syringe 36 and the patient via lines 20 and 50, and it has blocked off flow communication between the reservoir and line 40. Rotation of each three way valve element 214 in valves 208 and 210 by 180° reverses the connection established by the three way valve; i.e., syringe 38 would be connected to the patient by lines 42 and 50, and syringe 36 would be connected to the reservoir via lines 40 and 204.

Referring now to FIGS. 1, 2 and 8–10, a discussion of the actuation of the valves of directional adapter set 200 will be presented. The directional adapter set is mounted on the front of pump 10 on a projection 224 which has a pair of spring clips 225. The spring clips hold the directional adapter set by rigidly grasping T 212 at opposite sides of the stem of the T. This mounting of directional adapter set 200 on the front of the pump can best be seen in FIG. 10. As is also illustrated in FIG. 10, lines 40 and 42 are connected, respectively, to syringes 36 and 38 via female leur connections at the ends of lines 40 and 42. A pair of rotatable actuators 226 and 228 are located in the front of the housing of pump 10, and these actuators have elongated openings to receive the arrow shaped actuating handles 215 and 215' (associated with valve 210). Pins 230 and 232 are located at one end of each of these elongated openings to provide a locating reference for the notches 223 in the actuating handles. These locating pins can best be seen in FIG. 2, and the engagement of the locating pins with the notches in the actuating handle can best be seen in FIG. 10. The locating pins insure that the throughway valves must be properly positioned for synchronous action when the directional adapter set is mounted on the pump. Actuators 226 and 228 are mounted on gears 234 and 236 so that the actuators rotate as those gears are driven. Each of the gears 234 and 236 is driven by a gear segment which forms part of a Geneva type mechanism. Gear 238 has a radial slot 240 in which a pin 242 is located. A sliding movement between slot 240 and pin 242 occurs to drive gear 238 which in turn drives gears 234 and 236. Pin 242 is connected to an actuacting piston 244 in an actuating cylinder 246. Pneumatic actuating fluid is alternately delivered to opposite sides of piston 244 via supply lines 248 and 250 whereby piston 244 will alternately be driven from left to right and from right to left as seen in FIG. 8. That alternate linear movement of piston 244 results in alternate linear movement of pin 242, so that pin 242 will be driven in a straight line from left to right and then from right to left as seen in FIG. 9. That linear movement of pin 242 causes relative sliding motion between pin 242 and slot 240, whereby gear 238 is rotated about its center shaft 239. As seen in FIG. 9, leftward movement of pin 242 will drive gear 238 clockwise, thus resulting in counterclockwise rotation of gears 234 and 236; while rightward movement of pin 242 will drive gear 238 counterclockwise thus resulting in clockwise rotation of gears 234 and 236. The stroke of piston 244, and hence the linear throw of pin 242, is sufficient to result in alternate 180° rotations of gears 234 and 236. Thus, handles 215 and 215' and their respective valve cores 214 are rotated 180° each time to accomplish the previously described alternate connections of lines 40 and 42 and their respective syringes 36 and 38 to the reservoir and the patient.

As shown in FIG. 1, piston 16 is in its full rear position corresponding to a state of syringe 38 wherein the syringe has drawn a full charge of fluid from reservoir R; and piston 18 is shown in its full forward position corresponding to a state of syringe 36 wherein syringe 36 has delivered its full charge of fluid to a patient. Valve 208 is positioned to connect line 202 to line 42, and valve 210 is positioned to connect line 40 to the patient as the result of the positioning of piston 244. When the pistons 16 and 18 reach the position shown in FIG. 1 the control system (to be described hereinafter) causes the pistons 16 and 18 to move in the opposite directions; that is, piston 16 is driven to the right toward the full forward position and piston 18 is driven to the left toward the full rear position. Simultaneously the control system also causes piston 244 to shift whereby the position of valves 208 and 210 will change to connect line 42 to the patient and line 204 to line 40. The forward movement of piston 16 pushes plunger 34 into fully charged syringe 38 whereby the fluid charge in syringe 38 is discharged into tube 42. The fluid flowing in tube 42 is delivered to delivery line 50 and then on to the patient P. The new position of valve 208 permits this flow to delivery line 50. The new position of valves 208 and 210 prevents any reverse flow of the fluid charge from syringe 38 back to reservoir R or any flow from the reservoir to the patient. At the same time that piston 16 is moving forward, piston 18 is moving to its rearward position whereby rod 22 is withdrawing plunger 32 from syringe 36 to develop a suction force in syringe 36. As a result of this suction force, syringe 36 draws fluid from reservoir R through line 204 and line 40; the new position of valve 210 permitting this flow from reservoir R to syring 36. Similarly, because of the new position of valve 210, the suction in syringe 36 does not draw any fluid from delivery line 50 or the patient. Accordingly, as piston 16 moves to its full forward position the charge of fluid in syringe 38 is delivered at a uniform rate to the patient P while another charge of fluid is drawn from reservoir R and stored in syringe 36.

When the positions of the pistons 16 and 18 are reversed from that shown in FIG. 1, i.e. when piston 16 reaches the full forward position and piston 18 reaches the full rearward position, the control system reverses the direction of movement of pistons 16 and 18 to drive them back to the positions shown in FIG. 1. Simultaneously, the control system also shifts piston 244 back to the position shown in FIG. 1 to return valves 208 and 210 to the states shown in FIG. 1 to restore the line connections shown in FIG. 1. Rod 22 thus begins to move in the forward direction to push plunger 32 into syringe 36 whereby the charge of fluid in syringe 36 is delivered via tube 40 and valve 210 to delivery line 50 and thence to the patient P. The restored position of valve 210 permits this discharge flow from syringe 36 while the restored position of check valve 208 prevents any backflow to the reservoir. Simultaneously, the leftward movement of rod 20 withdraws plunger 34 from syringe 38 whereby a suction is drawn to pull a new charge of fluid from reservoir R through line 202 and valve 208 and tube 42 into syringe 38. The restored position of valves 208 and 210 prevents any flow of the fluid from reservoir R to the patient or to the reservoir from syringe 36 during the discharging of syringe 36.

The control system causes the pistons 16 and 18 to reciprocate at a desired rate of speed along with synchronous actuation of valves 208 and 210 (thru actuation of piston 244) whereby syringes 36 and 38 are alternately filled with fluid from reservoir R and discharged to patient P. Thus, a continuous and uninterrupted supply of fluid at a uniform rate is delivered to the patient. The fluid may be an anesthetic, medication, nutrients or any other desired material.

Still referring to FIG. 1, the control system has a pilot operated pneumatic valve 56 having pilots 58 and 60 to cause the valve to move between the two positions indicated by the standard notation in FIG. 1. A main supply valve 62 is connected to a main supply line 64, and valve 62 can be set to either connect line 64 to a main air supply or to vent line 64 through an exhaust as indicated. Supply line 64 has a first branch 66 which goes to valve 56 and serves as a supply to be delivered by the valve, and a second branch line 68 which is connected in turn through branch lines 70 and 72 to the pilot valves 58 and 60. Each of the branch lines 70 and 72 has a restriction 74 and 76 so that the venting or bleeding of one of the pilot valves will not affect the other. Delivery lines 78 and 80 run from valve 56 to chambers 24 and 28, respectively, in cylinders 12 and 14, and delivery lines 248 and 250, connected respectively to lines 80 and 78, run to opposite sides of piston 244 in cylinder 246. Depending on the position of valve 56, chambers 24 and 28 and the opposite sides of piston 244 are alternately pressurized and vented through valve 56. Bleed valves 82 and 84 are connected to pilot valves 58 and 60, respectively, to bleed the pilot valves in predetermined coordination with the positions of the pistons 16 and 18 and hence the condition or state of each of the plungers and syringes.

Bearing in mind that chambers 26 and 30 on the rear side of the pistons 16 and 18 are filled with an incompressible fluid and communicate via line 32, it can be seen that the rearward movement of one of the pistons 16 or 18 will transfer the incompressible fluid from its associated rear chamber to the associated rear chamber of the other piston to cause a movement of the other piston in the direction opposite to the movement of the one piston. The front sides of the pistons 16 and 18 are alternately pressurized pneumatically by actuating pressure delivered to the front chambers 24 and 28 from control valve 56 to effect the alternating and reciprocating motion of the pistons. Similarly, the opposite ends of piston 244 are alternately pressurized pneumatically to shift valves 208 and 210.

Assuming that the control valve is in the position shown in FIG. 1, the air supply will be delivered via lines 64 and 66 to line 78 and then to chamber 24 to actuate or power piston 16 and drive it to the left to its rearmost position. The air also drives piston 244 to the up position shown in FIG. 1. The rearward movement of piston 16 causes a transfer of the incompressible fluid from chamber 26 behind piston 16 to chamber 30 behind piston 18 whereby piston 18 is driven in the forward direction. Of course, as described above, those motions result in a filling of syringe 38 and a discharging of syringe 36. Piston 16 reaches its rearwardmost position at the same time as piston 18 reaches its forwardmost position. In the forwardmost position of piston 18 a shoulder 86 (see FIG. 2) contacts an actuating button 88 on bleed valve 82 to actuate the bleed valve. Bleed valve 82 is connected via bleed line 90 to pilot valve 60 whereby pilot valve 60 is vented to remove the pressure in line 72 from pilot valve 58. This venting of pilot valve 60 while pilot valve 58 remains pressurized causes valve 56 to be shuttled to the alternate position shown in FIG. 1 whereby delivery line 80 is connected to the supply line 66 and delivery line 78 is vented. This reversal of the pressure states of lines 78 and 80 results in the pressurizing of chamber 28 on the forward side of piston 18 and the venting of chamber 24 on the forward side of piston 16 whereby piston 18 is driven toward its rear position by the pneumatic pressure on its face and piston 16 is driven toward its forward position by the transfer of hydraulic fluid from chamber 30 behind piston 18 to chamber 26 behind piston 16. Piston 16 is thus driven to its forward position and piston 18 is driven to its rearward position. The reversal of the pressure states of lines 78 and 80 also simultaneously reverses the pressure loading on the ends of piston 244, thus driving piston 244 downward (with reference to FIG. 1) to shift the valves 208 and 210.

When piston 16 reaches its forward position a shoulder 92 (see FIG. 2) on rod 20 contacts an actuating button 92 on bleed valve 84 whereby pilot valve 58 is vented via line 95 and is no longer subject to the pressure line 72. The rearward movement of piston 18 resulted in the disengagement of shoulder 86 from actuating button 88 so that pilot valve 60 has become repressurized. The venting of pilot valve 58 while pilot valve 60 is pressurized results in a reshuttling of control valve 56 back to the position shown in FIG. 1 whereby the actuating pneumatic fluid is again delivered via line 78 to chamber 24 in cylinder 12 and chamber 28 of cylinder 14 is vented via line 80 so that the direction of movement of the pistons is again reversed. Similarly, the loading at the ends of piston 244 again reverses, and piston 244 moves to the up position of FIG. 1 to reshift the valves 208 and 210.

From the foregoing description, it can be seen that pilot operated valve 56 functions to alternately deliver actuating fluid to the two cylinders whereby the two pistons 16 and 18 continuously reciprocate 180° out of phase, i.e. they are moving in the opposite directions. The result is that each syringe is alternately drawing fluid from reservoir R and delivering fluid to the patient so that the patient always receives a continuous and uninterrupted supply of fluid. The valve 56 also functions to shift valves 208 and 210 in synchronism with the operation of the pistons 16 and 18 and the syringes to appropriately connect the syringes to the reservoir and to the patient.

A manually adjustable metering or control valve 96 is located in line 32. Metering valve 96 can be adjusted to vary the rate of transfer of the hydraulic fluid between chambers 26 and 30. The rate of transfer of the fluid between chambers 26 and 30 actually determines the speed at which the pistons reciprocate, and hence the rate of delivery of fluid to the patient. Thus, the rate of delivery of fluid from the infusion pump to the patient can be selected and adjusted as desired merely by changing the setting of valve 96. A fill valve 98 may also be included in line 32 to initially charge the system with the hydraulic fluid and to compensate for any losses.

In order to prevent air embolism, a filter 252 is placed in line 50 upstream of the patient. Filter 252 is a disposable intravenous micropore filter made by Millipore Corp., of Bedford, Massachusetts. The filter is a 0.22 micron filter which has a spiral chamber, and it has the characteristics that it will pass fluids but blocks air or other gases when wet. It will be understood that the presence of the filter is not absolutely mandatory, but it is a highly desirable safety feature.

Another safety feature is also effected as a result of the interseal piston bleed 15. If oil should leak past seal 17-17', it will be vented to atmosphere through bleed line 15, passage 21 and vent 23. Since there is no reservoir to replenish oil which has leaked, an oil leak will result in a shortening of the stroke of each of pistons 16 and 18. If the oil leak is severe enough, the stroke of the pistons will eventually be shortened to the point where the shoulders 86 will not contact the pilot actuating buttons 88 and 94. Once the pilot actuating buttons are no longer contacted, the pilot valves 58 and 60 will no longer be vented, and control valve 56 will no longer be shuttled. Thus, the unit will stop operating if the oil leak is sufficiently severe. If any such oil leak has occurred or is taking place, the sequencing frequency (i.e. the rate of reversal) of pistons 16 and 18 will decrease because the reduced stroke of the pistons will mean that shoulder 86 has to travel further before it contacts the actuating buttons 88 and 94. However, and most importantly, the rate of travel of pistons 16 and 18 will remain constant, with the result that the rate of delivery of fluid to the patient will remain constant. The maintaining of the constant rate of delivery of fluid to the patient notwithstanding this possible malfunction (i.e. oil leak) of the pump is an important safety feature since proper treatment of the patient requires a constant rate of delivery whenever fluid is supplied to the patient. This constant delivery rate will continue until the oil leak problem becomes so severe that the unit shuts down. The seals around pistons 16 and 18 and the interseal bleeds also prevent mixing of the fluids in the chambers on opposite sides of the pistons. This feature also contributes to maintaining the desired rate of operation of the pistons and the unit, since air can not get into the oil chambers whereby the stroke and rate of movement of the pistons would be adversely affected.

Figure 3:
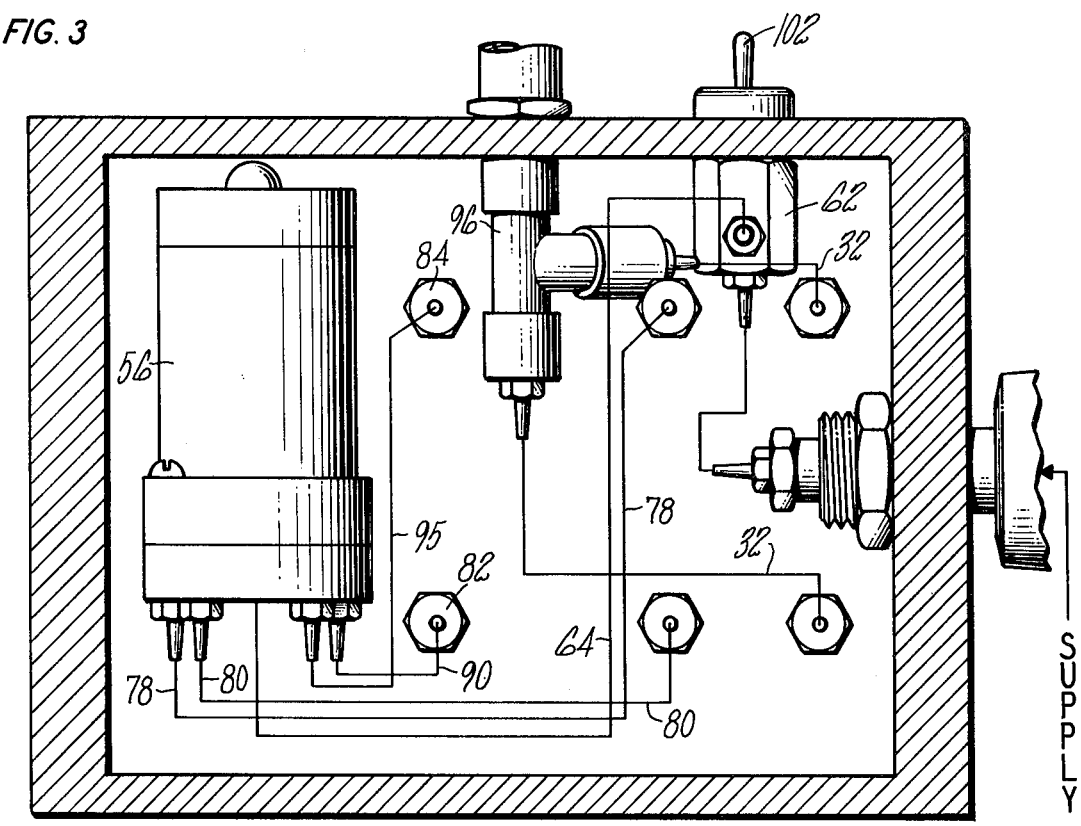
FIG. 3 is a sectional view of a modification of the pump of FIG. 2.

Referring now to FIGS. 2 and 3, some of the details of the infusion pump are shown in perspective and sectional details. As can be seen in FIG. 2, a pocket is formed in the end of each of the pistons with U-shaped slots 99 and 100 whereby the heads of the syringes are attached to the piston rods for movement with the piston rods. In the sectional view of FIG. 3, the casing of pump 10 is shown with valve 62 mounted thereon with an on/off switch 102 on the outside of pump 10. Supply line 64 leads to valve 56 which in turn has lines 78 and 80 leading to the inlets of their respective cylinders. Bleed lines 90 and 95 are also shown going from control valve 56 to the bleed valves 82 and 84. Metering valve 96 is also seen connected in line 32 between the entrances to the two oil chambers in the cylinders.

Figure 4:
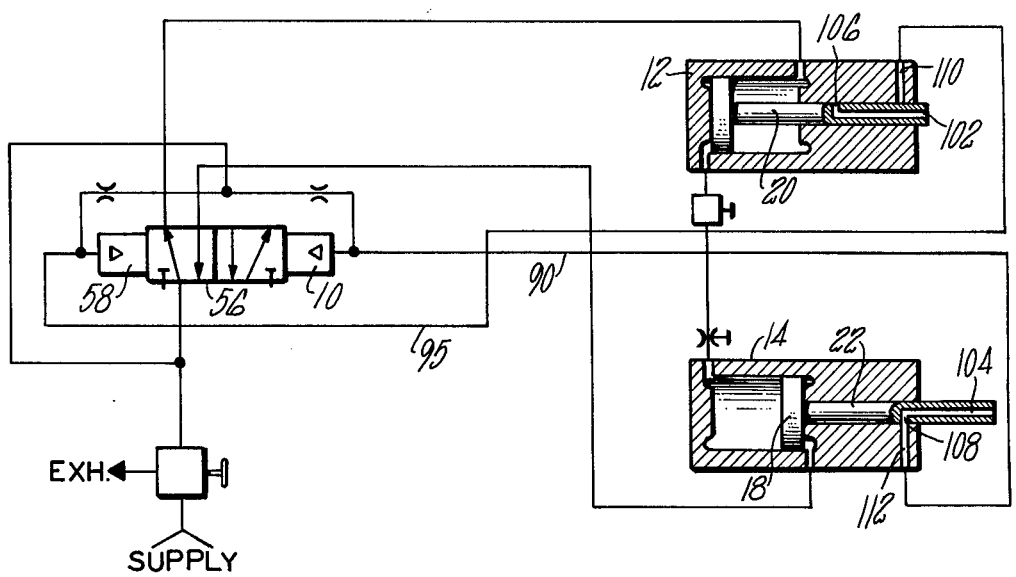
FIG. 4 is a schematic similar to FIG. 1 showing a modification.

Referring now to FIG. 4, a modified version of the system of FIG. 1 is shown. All of the elements of the FIG. 4 system are the same as those of FIG. 1 except those to be specifically described, and no discussion of those common parts is necessary. The only difference between the FIG. 4 configuration and the FIG. 1 system is the manner in which the pilot valves 58 and 60 are vented. In FIG. 4 the piston rods 20 and 22 each have central passageways 102 and 104 with radial inlets 106 and 108, all of which are in addition to passage 21 and bleed orifice 23 in each piston rod. The casings are also formed with radial passages 110 and 112 connected, respectively, to bleed lines 95 and 90. As each of the pistons 16 and 18 approaches the forward end of its stroke, the radial passage 106 or 108 in the rod comes into alignment with the radial passage in the cylinder casing. For example, as shown in FIG. 4, radial passage 108 of rod 22 comes into alignment with radial passage 112 of cylinder 14. When that alignment occurs bleed line 90 is vented through passage 104 to atmosphere through the end of rod 20. Similarly, when piston 16 reaches the forward end of its stroke, passages 106 and 110 come into alignment whereby bleed line 95 is vented through passage 102 to atmosphere through the end of rod 22.

The pump of the present invention can also function as an exchange transfusion pump merely by having the hydraulic and pneumatic fluids on opposite sides of the respective pistons. That is, the hydraulic fluid would be in the rear chamber of one cylinder and in the front chamber of the other cylinder, and the pneumatic fluid would be in the front chamber of that one cylinder and in the rear chamber of that other cylinder. For example, with the fluids in chambers 24 and 26 of cylinder 12, chamber 28 of cylinder 14 would be filled with the incompressible fluid with line 32 connected between chambers 26 and 28; and chamber 30 of cylinder 14 would receive the pneumatic fluid and be connected via delivery line 80 to control valve 56. This arrangement would cause the pistons to move in the same direction at the same time, thus resulting in the motion required to operate the device as an exchange transfusion pump. In this configuration proper control operation would require repositioning of bleed valve 82 to sense and be activated on the rearmost position of rod 22, the position of bleed valve 84 being unchanged.

While preferred embodiments have been shown and described, various modifications and substitutions may be made thereto without departing from the spirit and scope of the invention. Accordingly, it will be understood that the present invention has been described by way of illustration and not limitation.

What is claimed is:

1. An infusion pump including:

a first cylinder;

a second cylinder;

first piston means in said first cylinder dividing said first cylinder into first and second chambers;

second piston means in said second cylinder dividing said second cylinder into first and second chambers;

first rod means connected to said first piston means and extending out of said first cylinder, said first rod means being adapted for connection to the plunger of a syringe;

second rod means connected to said second piston means and extending out of said second cylinder, said second rod means being adapted for connection to the plunger of a syringe;

hydraulic conduit means connecting said first chamber of said first cylinder to said first chamber of said second cylinder for fluid communication therebetween;

incompressible fluid means in said first chamber of each of said cylinders and in said hydraulic conduit means;

actuator means for positioning valve means to control the flow of a fluid to and from said syringes;

third cylinder means;

third piston means in said third cylinder means, said third piston means being operatively connected to said actuator means;

delivery means for delivering fluid under pressure to said second chambers of said first and second cylinders and to said third cylinder means; and control means for alternately delivering fluid through said delivery means to the second chamber of one of said cylinders to activate the piston means associated therewith and transfer fluid from the first chamber of said one cylinder to the first chamber of the other cylinder and then to the second chamber of the other of said cylinders to activate the piston means associated therewith and transfer fluid from the first chamber of said other cylinder to the first chamber of said one cylinder, said control means further alternately delivering fluid under pressure to opposite sides of said third piston means to cause said third piston means to operate said actuator means in synchronism with said first and second piston means.

2. An infusion pump as in claim 1 including:

control means in said hydraulic conduit means for selectively varying the rate of transfer of hydraulic fluid between said first chambers.

3. An infusion pump as in claim 1 wherein said control means includes:
pilot operated valve means for directing pneumatic fluid under pressure to one or the other of said second chambers; and
sensing means for sensing the movement of said first and second piston means to actuate said pilot operated valve means to switch the direction of pneumatic fluid to one or the other of said second chambers.

4. An infusion pump as in claim 1 wherein:
said delivery means includes first delivery line means connected between said control means and said second chamber of said first cylinder and one side of said third piston means, and second line means connected between said control means and said second chamber of said second cylinder and the other side of said third piston means; and wherein
said pilot operated valve means alternately connects said first and second delivery line means to a source of pressurized pneumatic fluid.

5. An infusion pump as in claim 1 including:
sensing means for sensing the movement of said first and second piston means, said sensing means actuating said control means upon the sensing of predetermined positions of said pistons to repeatedly switch the delivery of said fluid from one of said second chambers to the other of said second chambers, and to switch the delivery of said fluid to said third cylinder means.

6. An infusion pump as in claim 5 wherein:
said positions of said first and second piston means are commensurate with the states of fluid containment of the syringes to which said rod means are adapted for connection.

7. An infusion pump including:
a first cylinder;
a second cylinder;
first piston means in said first cylinder dividing said first cylinder into first and second chambers;
second piston means in said second cylinder dividing said second cylinder into first and second chambers;
first rod means connected to said first piston means and extending out of said first cylinder, said first rod means being adapted for connection to the plunger of a syringe;
second rod means connected to said second piston means and extending out of said second cylinder, said second rod means being adapted for connection to the plunger of a syringe;
hydraulic conduit means connecting said first chamber of said first cylinder to said first chamber of said second cylinder for fluid communication therebetween;
incompressible fluid means in said first chamber of each of said cylinders and in said hydraulic conduit means;
a pair of rotatably mounted actuators, each of said actuators having a part shaped to engage a part of a valve to be actuated to control the flow of a fluid to and from said syringes;
power means for operating said actuators;
delivery means for delivering fluid under pressure to said second chambers of said first and said second cylinders and to said power means; and
control means for alternately delivering fluid through said delivery means to the second chamber of one of said cylinders to activate the piston means associated therewith and transfer fluid from the first chamber of said one cylinder to the first chamber of the other cylinder and then to the second chamber of the other of said cylinders to activate the piston means associated therewith and transfer fluid from the first chamber of said other cylinder to the first chamber of said one cylinder, said control means also delivering fluid to said power means to operate said actuators in synchronism with said piston means.

8. An infusion pump as in claim 7 wherein:
said power means moves linearly; and including
means to convert the lineal motion of said power means to rotary motion for said actuators.

9. An infusion pump as in claim 7 further including:
control means in said hydraulic conduit means for selectively varying the rate of transfer of hydraulic fluid between said first chambers.

10. An infusion pump as in claim 7 wherein said control means includes:
pilot operated valve means for directing pneumatic fluid under pressure to one or the other of said second chambers; and
sensing means for sensing the movement of said first and second piston means to actuate said pilot operated valve means to switch the direction of pneumatic fluid to one or the other of said second chambers.

11. An infusion pump as in claim 7 including:
sensing means for sensing the movement of said first and second piston means, said sensing means actuating said control means upon the sensing of predetermined positions of said pistons to repeatedly switch the delivery of said fluid from one of said second chambers to the other of said second chambers, and to switch the delivery of said fluid to said power means.

12. An infusion pump as in claim 11 wherein:
said positions of said first and second piston means are commensurate with the states of fluid containment of the syringes to which said rod means are adapted for connection.

13. An infusion pump including:
a first cylinder;
a second cylinder;
first piston means in said first cylinder dividing said first cylinder into first and second chambers;
second piston means in said second cylinder dividing said second cylinder into first and second chambers;
first rod means connected to said first piston means and extending out of said first cylinder, said first rod means being adapted for connection to the plunger of a syringe;
second rod means connected to said second piston means and extending out of said second cylinder, said second rod means being adapted for connection to the plunger of a syringe;
hydraulic conduit means connecting said first chamber of said first cylinder to said first chamber of said second cylinder for fluid communication therebetween;
incompressible fluid means in said first chamber of each of said cylinders and in said hydraulic conduit means;
actuator means for positioning valve means to control the flow of a fluid to and from said syringes;

power means for operating said actuator means, said power means including:
a third cylinder;
a linearly movable piston disposed in said third cylinder;
an actuating rod extending from said linearly movable piston and out of said third cylinder;
first gear means mounted for rotation and having a radial slot engaged by said actuating rod; and
second gear means driven by said first gear means, said second gear means being connected to said actuator means for controlling the operation of said actuator means;
delivery means for delivering fluid under pressure to said second chambers of said first and second cylinders and to said third cylinder of said power means to cause movement of said power means linearly movable piston;
control means for alternately delivering fluid through said delivery means to the second chamber of one of said cylinders to activate the piston means associated therewith and transfer fluid from the first chamber of said one cylinder to the first chamber of the other cylinder and then to the second chamber of the other of said cylinders to activate the piston means associated therewith and transfer fluid from the first chamber of said other cylinder to the first chamber of said one cylinder, said control means also delivering fluid to said power means third cylinder to operate said power means linearly movable piston thereby operating said actuator means in synchronism with said piston means; and
means for mounting directional adapter set means on said pump, said directional adapter set means including the valve means which controls fluid flow to and from said syringes;
said actuator means having shaped parts to operatively engage corresponding parts on said valve means.

14. An infusion pump including:
a first cylinder;
a second cylinder;
first piston means in said first cylinder dividing said first cylinder into first and second chambers, said first piston means including:
a first cylindrical piston element;
a radial bleed from the periphery of said first cylindrical piston element; and
seal means on the periphery of said first cylindrical piston element, said seal means straddling said radial bleed;
second piston means in said second cylinder dividing said second cylinder into first and second chambers, said second piston means including:
a second cylindrical piston element;
a radial bleed from the periphery of said second cylindrical piston element; and
seal means on the periphery of said second cylindrical piston element, said seal means straddling said radial bleed;
first rod means connected to said first piston means first cylindrical piston element, said first rod means extending out of said first cylinder, said first rod means including a passage for venting the radial bleed in said first cylindrical piston element to atmosphere, said first rod means being adapted for connection to the plunger of a syringe;
second rod means connected to said second piston means cylindrical piston element, said second rod means extending out of said second cylinder, said second rod means including a passage for venting the radial bleed in said second cylindrical piston element to atmosphere, said second rod means being adapted for connection to the plunger of a syringe;
hydraulic conduit means connecting said first chamber of said first cylinder to said first chamber of said second cylinder for fluid communication therebetween;
incompressible fluid means in said first chamber of each of said cylinders and in said hydraulic conduit means;
actuator means for positioning valve means to control the flow of a fluid to and from said syringes;
power means for operating said actuator means;
delivery means for delivering fluid under pressure to said second chambers of said first and second cylinders and to said power means; and
control means for alternately delivering fluid through said delivery means to the second chamber of one of said cylinders to activate the piston element associated therewith and transfer fluid from the first chamber of said one cylinder to the first chamber of the other cylinder and then to the second chamber of the other of said cylinders to activate the piston element associated therewith and transfer fluid from the first chamber of said other cylinder to the first chamber of said one cylinder, said control means also delivering fluid to said power means to operate said actuator means in synchronism with said piston elements.

15. An infusion pump as in claim 14 wherein said second gear means includes:
a pair of spaced apart gears attached to a pair of spaced apart actuators.

16. A directional adapter set for use with an infusion pump, the directional adapter set including:
a first three way valve, said first valve including a valve element rotatable 180° between first and second positions, said first valve having a flow passage therethrough;
a second three way valve, said second valve including a valve element rotatable 180° between first and second positions, said second valve having a flow passage therethrough;
handle means connected to each of said valve elements for moving said valve elements;
first conduit means connected to said first valve and adapted to be connected to a syringe through the flow passage therethrough;
second conduit means connected to said second valve and adapted to be connected to a syringe through the flow passage therethrough;
third conduit means connected to said first and second valves and adapted to be connected to a patient;
fourth conduit means connected to said first valve and adapted to be connected to a fluid reservoir through said first valve flow passage; and
fifth conduit means connected to said second valve and adapted to be connected to a fluid reservoir through said second valve flow passage;
said first conduit means being connected to said third conduit means through said first valve flow passage and blocked from fluid communication with said fourth conduit means when said first valve is in the first position, said second conduit means being connected to said fifth conduit means through said second valve flow passage and being blocked from fluid communication with said third conduit means when said second valve is in the first position, said first conduit means being connected to said fourth conduit means through said first valve flow passage and being blocked from fluid communication with said third conduit means when said first valve is in the second position, said second conduit means being connected to said third conduit means through said second valve flow passage and being blocked from fluid communication with said fifth conduit means when said second valve is in the second position.

17. The directional adapter as in claim 16 wherein said handle means includes:
shaped handle means connected to each of said valve elements to move said valve elements, said handle means being adapted to engage a shaped valve actuator.

18. A directional adapter set as in claim 17 wherein:
said shaped handle means are each in the form of an arrow, with the head of each arrow pointing to a conduit with which fluid communication is established through the valve.

* * * * *